US011298432B2

(12) United States Patent
Barre et al.

(10) Patent No.: US 11,298,432 B2
(45) Date of Patent: Apr. 12, 2022

(54) METHOD FOR PREPARING A MARKED PURINE DERIVATIVE, SAID DERIVATIVE AND USES THEREOF

(71) Applicant: Commissariat a l'energie atomique et aux energies alternatives, Paris (FR)

(72) Inventors: Louisa Barre, Soliers (FR); Patrice Marchand, Fresney le Vieux (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 143 days.

(21) Appl. No.: 14/633,067

(22) Filed: Feb. 26, 2015

(65) Prior Publication Data
US 2015/0238640 A1  Aug. 27, 2015

Related U.S. Application Data

(62) Division of application No. 12/810,965, filed as application No. PCT/EP2008/068244 on Dec. 23, 2008, now abandoned.

(30) Foreign Application Priority Data

Jan. 3, 2008 (FR) ...................................... 08 50014

(51) Int. Cl.
*A61K 51/00* (2006.01)
*A61M 36/14* (2006.01)
*A61K 51/04* (2006.01)
*C07B 59/00* (2006.01)
*C07D 473/04* (2006.01)
*C07D 473/40* (2006.01)

(52) U.S. Cl.
CPC ........ *A61K 51/0491* (2013.01); *C07B 59/005* (2013.01); *C07D 473/04* (2013.01); *C07D 473/40* (2013.01)

(58) Field of Classification Search
CPC .................................................. A61K 51/0491
USPC ...................................................... 424/1.73
See application file for complete search history.

(56) References Cited

U.S. PATENT DOCUMENTS

| 2005/0106101 A1 | 5/2005 | Purohit et al. |
| 2005/0244331 A1 | 11/2005 | Abraham |
| 2009/0105184 A1* | 4/2009 | Radu et al. ...................... 514/45 |
| 2009/0162283 A1 | 6/2009 | Bando et al. |

FOREIGN PATENT DOCUMENTS

| EP | 1 956 013 A1 | 8/2008 |
| FR | 2 841 554 A1 | 1/2004 |
| JP | 2000-510816 | 8/2000 |
| JP | 2003-500450 | 1/2003 |
| JP | 2007-527423 | 9/2007 |
| WO | WO 94/12514 A1 | 6/1994 |
| WO | WO 97/14679 A2 | 4/1997 |
| WO | WO 00/72849 A1 | 12/2000 |
| WO | WO 03/099342 A1 | 12/2003 |
| WO | WO 2005/044312 A1 | 5/2005 |
| WO | WO 2005/056571 A1 | 6/2005 |
| WO | WO 2005/082425 A1 | 9/2005 |
| WO | WO 2007/063946 A1 | 6/2007 |
| WO | WO 2008/140616 A2 | 11/2008 |

OTHER PUBLICATIONS

Keating et al. Hematol. Cell Ther. 1996, 38, S83-S91.*
Roberts et al. Clin. Lymphoma 2002, 3, 184-188.*
Lee et al. Biochem Biophys. Res. Comm. 2007, 357, 620-626.*
Seam et al. Blood 2007, 110, 3507-3516. (Year: 2007).*
Dhilly et al. Mol. Imaging Biol. 2014, 16, 118-126. (Year: 2014).*
Jacobson K.A. and Gao Z.-G., "Adenosine receptors as therapeutic targets," *Nat. Rev. Drug Discovery* 2006, 5, 247.
Robins M.J. and Uznanski B., "Nucleic acid related compounds. 34. Non-acqueous diazotization with tert-butyl nitrite. Introduction of fluorine, chlorine, and bromine at C-2 of purine nucleosis," 1981, *Can. J. Chem.* 59, 2608.
Horti et al., "Synthesis of 2-[$^{18}$F]fluoroadenosine (2-[$^{18}$F]FAD) as potential radiotracer for studying malignancies by PET," 2006, *J. Labelled Compd. Radiopharm.*, 49, 811.
Hocek et al., "Highly Methylated Purines and Purinium Salts as Analogues of Heteromines," 2005, *Eur. J. Org. Chem.* 14, 3026.
Irie et al., "Synthesis of $^{18}$F-6-fluoropurine and $^{18}$F-6-fluoro-9-β-D-ribofuranosylpurine," 1982, *Int. J. Appl. Radiat. Isot.* 33(6), 445.
Wanner et al., "2-Nitro Analogues of Adenosine and 1-Deazaadenosine: Synthesis and Binding Studies at the Adenosine $A_1$, $A_{2A}$ and $A_3$ Receptor Subtypes," *Med. Chem. Lett.* 10.. 2000b, 2141-2144.
Wanner and Koomen, "Synthesis and properties of 2-nitrosoadensine," *J. Chem. Soc., Perkin Trans 1*, 2001, 1908-1915.
Deghati et al., "Regioselective nitration of purine nucleosides: synthesis of 2-nitroadenosine and 2-nitroinosine," *Tetrahedron lett.*, 41, 2000, 1291-1295.
Nowak et al., "Nucleic Acid Related Compounds. 127. Selective N-Deacylation of N,O-Peracylated Nucleosides in Superheated Methanol," *J. Org. Chem.* 70, 2005, 7455-7458.
Ishido et al., "Partial Protection of Carbohydrate Derivatives. Part 1. Specific N-Debenzoylation of Fully Benzoylated Adenosine and Cytidine with Phenols and Alcohols; Active N-Benzoyl Groups," *J. Chem. Soc. Perkin Trans. 1*, 1977, 657-660.

(Continued)

*Primary Examiner* — Michael G. Hartley
*Assistant Examiner* — Sean R Donohue
(74) *Attorney, Agent, or Firm* — Miles & Stockbridge, P.C.

(57) ABSTRACT

The present invention relates to a method for preparing a 2-fluoropurine marked with the radioisotope $^{18}$F comprising a fluorination step for a 2-nitropurine derivative. The present invention comprises a 2-fluoropurine derivative marked with the radioisotope $^{18}$F which can be obtained by or during a method according to the invention and its various uses.

6 Claims, 5 Drawing Sheets

(56) References Cited

OTHER PUBLICATIONS

Braendvang et al., "A Novel Method for the Introduction of Fluorine into the Purine 2-Position: Synthesis of 2-Fluoroadenosine and a Formal Synthesis of the Antileukemic Drug Fludarabine," 2006, *Synthesis. 18*, 2993.

Gimisis et al., "Generation of C-1' Radicals through a β-(Acyloxy)alkyl Rearrangement in Modified Purine and Pyrimidine Nucleosides," 1998, *Tetrahedron*, 54, 573.

Ding, Y.S., et al., "No-Carrier-Added (NCA) Aryl [$^{18}$F]fluorides via the Nucleophilic Aromatic Substitution of Electron-Rich Aromatic Rings," *J. Fluorine Chem.*, 1990, vol. 48, No. 2, Elsevier, pp. 189-205.

Coenen, H.H., "Fluorine-18 Labeling Methods: Features and Possibilities of Basic Reactions," 2005, *Ernst Schering Research Foundation Workshop*, vol. 62, Springer, pp. 15-50.

Kilbourn, M.R., "Fluorine-18 Labeling of Radiopharmaceuticals," 1990, *National Academy Press*, Washington, DC, pp. 55-63.

Briard et al., J. Labelled Compd Radipharm. 2004; 47; 217-232.

Horti et al., J. Labelled Cmpd Radipharm. 2006, 49, 811-815.

Wanner et al., Bioorg. Med. Chem. Lett. 2000, 10, 2141-2144.

\* cited by examiner

METHOD FOR PREPARING A MARKED PURINE DERIVATIVE, SAID DERIVATIVE AND USES THEREOF

TECHNICAL FIELD

The present invention relates generally to marked labelled chemical compounds and, particularly, to marked purine derivatives.

More particularly, the present invention relates to a method for marking purine derivatives with fluor-18. The present invention also relates to new purine derivatives marked labelled with fluor-18 and reaction intermediates thusly obtained and, more particularly, to purine derivatives marked in position 2 of the aromatic ring by fluor-18.

The present invention also relates to the different uses of these new purine derivatives and reaction intermediates marked with fluor-18 in PET imaging, research, therapeutic evaluation, or diagnosis.

PRIOR ART

Positron emission tomography (hereinafter "PET"), a non-invasive imaging method for the in vivo assessment of drug distribution and interaction with biochemical target systems, is well adapted to the exploration of different physiological and physiopathological functions in Man.

This tool has rapidly become essential in oncology, neurobiology, and cardiology. At the present time, the challenge in the field of PET is to produce and offer, at a moderate cost, PET probes that can be used in numerous applications. This objective can be achieved by devising compounds labelled with a positron emitter and being efficiently produced.

Among the potential PET probes, the purine derivatives, comprising in particular nucleosides and nucleotides, are the object of a growing interest, certain of these derivatives having been shown to have biological activities in a variety of areas. Furthermore, in the last few years, growing efforts have been made with respect to the elaboration of ligands of the adenosine receptors, leading to the development of promising agents based on purine or adenosine entities (Article of Jacobson K. A. and Gao Z.-G. *Nat. Rev. Drug Discovery* 2006, 5, 247).

Several compounds having purine or pyrimidine groups have already been developed as markers in PET imaging, and most of the strategies used have involved marking either the side chain or the sugar with a radioisotope. Radiomarked purines and adenosines having a covalent link between the ring and the isotope have previously been described; they have in particular been obtained by using as a radioisotope either $^2$H, $^3$H, $^{15}$N, $^{13}$C and $^{11}$C, or even $^{18}$F.

The carbon $^{11}$C labeling has largely been studied, particularly in terms of biological data, and patented (International Application WO 03/099342). The [$^{11}$C]-adenosine monophosphate has been achieved from [$^{11}$C]-formaldehyde after 34 min, for a formaldehyde yield of 2.4%. However, this method presents some disadvantages: a low yield despite a proper synthesis time and the short half-life of the carbon $^{11}$C ($t_{1/2}$=20.4 min), which limits its applications to examinations carried out over short periods of time. Another object of this application relates to the synthesis of 2-[$^{18}$F]-fluoroadenosine via a nucleophilic substitution reaction of fluor-18 on the corresponding diazonium salt. This method, inspired by conventional syntheses (Article of Robins M. J. and Uznanski B., 1981, *Can. J. Chem.* 59, 2608), has appeared not to be adapted for the synthesis of 2-[$^{18}$F]-fluoroadenosine, and the inventor of the application has recently reported that this method was unfeasible (Article of Horti at al., 2006, *J. Labelled Compel Radiopharm.*, 49, 811).

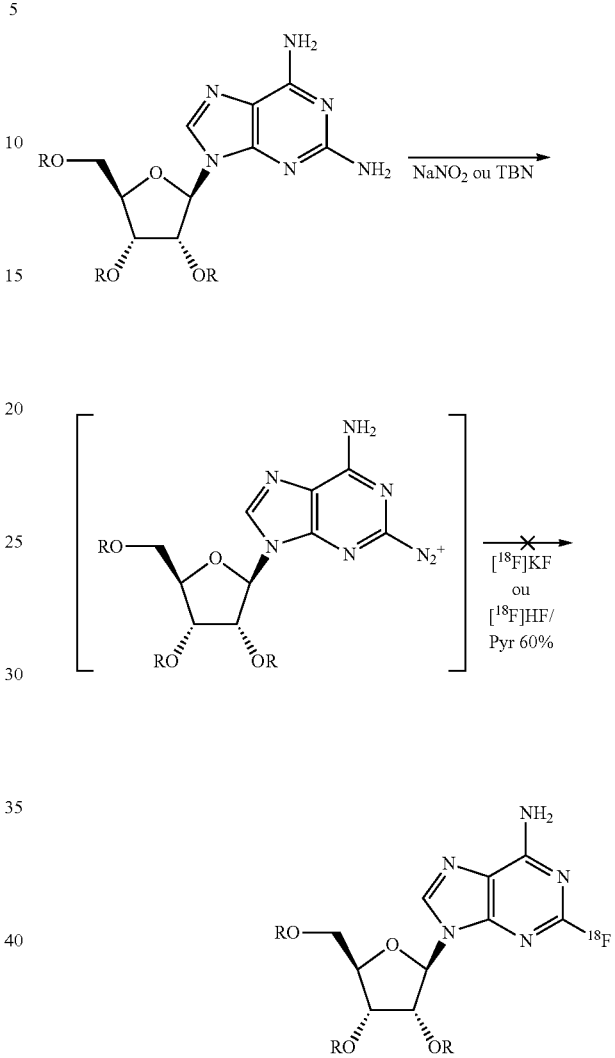

Diagram 1: Unfeasibility of the method described in the international application WO 03/099342 (R representing hydrogen or a protecting group), as mentioned in the Article of Horti et al., 2006.

International Application WO 2005/044312 in the name of Bristol-Myers Squibb Company, is directed to the synthesis of 2-[$^{18}$F]-fluoroadenosine (2-[$^{18}$F]FAD) from the corresponding 2-N,N,N-(trimethylammonium) adenosine triflate. It is well known that 2-N,N,N-(trimethylammonium) adenosine triflate has never been isolated or even ever observed. Presently, the starting material is a hypothetical compound for which the synthesis has been unsuccessful. It has been demonstrated that the corresponding ammonium could not be obtained by using the trimethylamine (Article of Robins M. J. and Uznanski B., 1981, *Can. J. Chem.* 59, 2601). The attempts to generate the corresponding ammonium via the alkylation of a secondary amine also failed since the alkylation always occurs in the area of the 7 or 9 position of the purine core, and not in the 2 position (Article of Hocek et al., 2005, *Eur. J. Org. Chem.* 14, 3026).

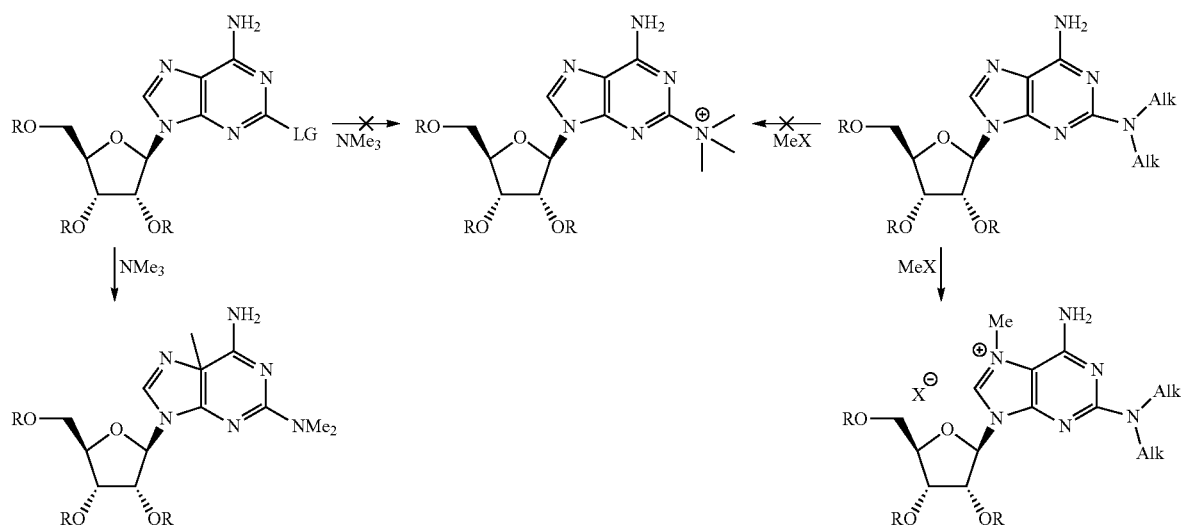

Diagram 2: Inefficient synthesis of the derivatives of 2-N, N,N-(trialkylammonium)-adenosine. The meaning of the symbols used in the diagram 2 is the following: R=H or a protecting group; LG=leaving group; X=I, OTf and Alk=alkyl group.

The synthesis of the 2-[$^{18}$F]-fluoroadenosine (2-[$^{18}$F] FAD) as a potential radiolabel has been made either from the corresponding 2-iodoadenosine, or from the corresponding 2-fluoroadenosine (isotopic substitution). In both cases, starting from unprotected nucleosides, the reaction produces marked compounds in/with low yields (0.5% and 5% from the iodized or fluorinated precursors, respectively) and with very low, specific radioactivities (Article of Horti et al., 2006, *J. Labelled Compd*. Radiopharm. 49, 811).

European Patent Application EP 1 956 013 in the name of Fujifilm Pharma and Daiichi Sankyo, proposes to prepare a compound carrying an imidazopyrimidine group marked with fluor-18 from a compound carrying a nitrated imidazopyrimidine. On the one hand, the reaction scheme is entirely theoretical and without any experimental justification. On the other hand, the possible feasibility of the marking on imidazopyrimidine groups such as disclosed in this document does not foretell at all the possibilities and marking conditions of other different heterocycles such as purines.

The preparation of the 2-fluoro-9-benzylpurine marked with fluor 18 has also been disclosed by Irie et al. (T. Irie, K. Fukushi, O. Isnoue, T. Yamasaki, T. Ido, T. Nozaki *Int. J. Appl. Radiat. Isot.*, 33, 1982, 633-636) from silver fluoride marked with fluor-18. The method disclosed necessitates the use of silver fluoride in excess and yields only 5.4-6.7%. This method, which is quite inefficient, is unsuitable for the development of a radiopharmaceutical.

Marking in the 6 position has also been disclosed using the [$^{18}$F]$^-$ fluoride ion via a nucleophilic displacement of the corresponding trimethyl ammonium salt. Rather than the 2 position, the 6 position of the purine can be functionalized via its ammonium (Article of Irie, et al., 1982, *Int. J. Appl. Radial. Isot.* 33(6), 445).

Despite the rising interest in these powerful agents for PET imaging, no efficient method of marking a molecule comprising a purine nucleus in 2 position of the aromatic ring by using [$^{18}$F] fluorine has ever been described.

Furthermore, the introduction of a halogen atom in the 2 position of the adenosine (and adenine-based derivatives) is known to augment the biological half-life of the molecule and, consequently, its effects mostly via the inhibition of the enzymatic activity of the adenosine deaminase. Therefore, considering the need for new PET agents, the potential of marked nucleosides for the diagnosis of cancers or the evaluation of drugs and treatment efficiency, and the increasing interest in adenosine receptors, there is an obvious need for a more efficient strategy for radiolabeling the purines, and, in particular, in the 2 position of the aromatic ring. Consequently, an efficient radiosynthesis of 2-[$^{18}$F]fluoropurine derivatives would be significant progress in the field of PET imaging.

DESCRIPTION OF THE INVENTION

The present invention allows for resolving the previously described technical problems, and for providing a solution to the aforementioned need, by proposing an original method for marking the purines and purine derivatives (such as the nucleosides) by using a [$^{18}$F] fluorine atom.

In what precedes and what follows, the atom numbering system generally accepted for the purine nucleus and shown hereinafter is used:

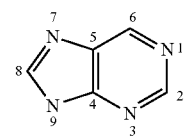

The present invention proposes an easy and very efficient means for preparing the derivatives of 2-[$^{18}$F] fluoropurines, protected or not. The method, which is an object of the invention is particularly efficient in the case of adenosine and adenine derivatives such as, by way of non-limiting examples, the nucleosides.

The method of the present invention is remarkable in that this reliable method can easily apply to different derivatives of 2-nitropurines and, due to the simplicity and efficiency of the method of the invention, an appropriate and fully automated method could be developed.

The present invention relates to a method for preparing a 2-fluoropurine marked with the $^{18}$F radioisotope, comprising a fluorination step of a 2-nitropurine derivative.

More particularly, the fluorination step of the method of the invention involves making a 2-nitropurine derivative react with a source of [$^{18}$F] marked-fluoride F ions to obtain the 2-[$^{18}$F] fluoropurine derivative.

Therefore, the present invention relates to a method for preparing a 2-fluoropurine derivative marked with the $^{18}$F radioisotope, comprising a fluorination step consisting in reacting a 2-nitropurine derivative, optionally protected with a source of [$^{18}$F] marked-fluoride F ions, optionally followed by a deprotection step, to obtain the 2-[$^{18}$F]fluoropurine derivative.

Interestingly, the method according to the invention can be implemented with a very large deficiency of fluorine relative to the 2-nitropurine derivative, which makes this method usable in the chemistry of fluorine-18. Advantageously, the fluorine can be used in quantities that are less than or equal to $10^{-1}$, or even less than or equal to $10^{-2}$ equivalents with respect to the 2-nitro-purine derivative.

In the context of the invention, "2-fluoropurine derivative marked with the $^{18}$F radioisotope" refers to a compound comprising a purine nucleus, and having a formula (Ia)

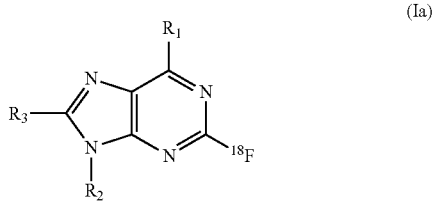

in which
$R_1$ represents H, an optionally substituted alkyl group, an optionally substituted aryl group, a $NR_4R_5$ group;
$R_2$ represents H, an optionally substituted alkyl group, an optionally substituted aryl group, an optionally substituted furanose group, or an optionally substituted pyranose group;
$R_3$ represents H, an optionally substituted alkyl group, an optionally substituted aryl group, a halogen, a —$OR_8$ group or a —$SR_8$ group, with $R_8$ representing H, an optionally substituted alkyl group, an optionally substituted aryl group,
$R_4$ and $R_5$ independently represent H, an electroattractive group, an optionally substituted alkyl group, an optionally substituted aryl group, an optionally substituted acyl group, an optionally substituted sulfinyl group, or an optionally substituted sulfonyl group.

Derivatives of the 2-fluoropurine marked with the $^{18}$F radioisotope advantageously prepared by the method of the present invention are compounds of the formula (Ia) in which $R_1$ represents a $NR_4R_5$ group such as previously defined and, more particularly, compounds of the formula (Ia) in which R represents a $NH_2$ group.

Furanose groups advantageously implemented in the context of the present invention are the ribofuranose and arabinofuranose groups.

In the context of the present invention, "alkyl group" refers to a cyclic, branched, or linear alkyl group, optionally substituted, having from 1 to 20 carbon atoms, especially from 1 to 10 carbon atoms, in particular, from 1 to 8 carbon atoms, more particularly, from 1 to 6 carbon atoms.

In the context of the invention, "aryl group" refers to a mono- or polycyclic aromatic group, optionally substituted, having from 6 to 20 carbon atoms, especially from 6 to 14 carbon atoms, and particularly from 6 to 8 carbon atoms. By way of examples of the aryl group according to the invention, the following groups are included: phenyl, naphth-1-yl, naphth-2-yl, anthracen-9-yl, 1,2,3,4-tetrahydronaphth-5-ylc and 1,2,3,4-tetrahydronapht-6-yle.

In the context of the present invention, "acyl group" refers to a linear or branched acyl group, optionally substituted, having from 1 to 10 carbon atoms, in particular, from 1 to 8 carbon atoms, more particularly, from 1 to 6 carbon atoms.

In the context of the present invention, "electroattractive group" refers to a group chosen from among the $NO_2$ and nitrile groups, imide and imine derivatives, a carbonyl —C(=O)—R group, a —O—C(=O)—R group, in which R is a hydrogen atom, an OH group, an alkyl group, an alkoxy group, or an aryl group, optionally substituted.

In the context of the present invention, "sulfinyl group" refers to a group having the RSO— formula, R being an alkyl or aryl group such as previously defined.

In the context of the present invention, "sulfonyl group" refers to a group having the $RSO_2$— formula, R being an alkyl or aryl group such as previously defined.

In the context of the invention, "optionally substituted" means a radical substituted with one or several groups chosen from among: an alkyl group, an alkoxy group, a halogen, a hydroxy, a cyano, a trifluoromethyl, a nitro or a protecting group.

In the context of the present invention, "alkoxy group" means an oxygen atom substituted with an alkyl such as previously defined.

In the context of the invention, "halogen" stands for a fluorine, chlorine, bromine, or iodine.

The 2-nitropurine derivative implemented in the context of the invention has the formula (Ib)

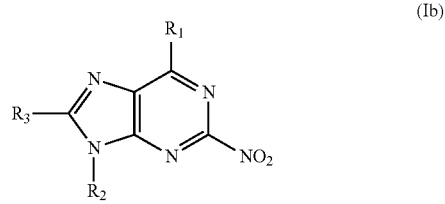

with $R_1$, $R_2$ and $R_3$ being previously defined. Such compounds are readily available to those of ordinary skill in the art. International Application WO 2005/05657, the Article of Wanner et al., Med. Chem. Lett. 10, 2000b, 2141-2144, the Article of Wanner et Koomen, J. Chem. Soc., Perkin Trans 1, 2001, 1908-1915 and the Article of Degati et al., Tetrahedron lett., 41, 2000, 1291-1295 propose particular methods of synthesis of compounds responding to the formula (Ib). It is easy for one having ordinary skill in the art to prepare, from these teachings, all of the compounds of formula (Ib).

In the fluorination step of the method according to the invention, the source of [$^{18}$F] marked fluoride ions comprises said fluoride ions and a counter-ion, chosen from among large cations and small cations.

A large cation advantageously Implemented in the context of the present invention is tetrabutylammonium ($Bu_4N^+$).

Tetrabutylammonium fluoride marked with the radioisotope $^{18}$F (Bu$_4$N[$^{18}$F]F) is conventionally prepared by using Bu$_4$NOH or Bu$_4$NHCO$_3$.

Non limiting examples of small cations include potassium, sodium and lithium cations. Said small cations can advantageously be quenched, stabilized, for example, by a cryptand or crown ether, etc., said cryptand or crown ether being adapted to the small cation employed. An example of cryptand which can be implemented in the context of the present invention is the product KRYPTOFIX® K$_{222}$: (4,7,13,16,21,24-hexaoxa-1,10-diaza bicyclo[8.8.8]hexacosane) which quenches, for example, the potassium ion.

The counter-ion or cation can be in the form of any salt, for example, it can be K$_2$CO$_3$, K$_2$SO$_4$ or potassium oxalate in the case of potassium. It must be noted that the salt and, in particular, K$_2$CO$_3$, should be advantageously used, during the fluorination step, at a quantity inferior or equal to 1 mg/mg of 2-nitropurine derivative, particularly a quantity less than or equal to 0.6 mg/mg of 2-nitropurine derivative and, in particular, a quantity less than or equal to 0.1 mg/mf of 2-nitropurine derivative.

The fluorination step of the method according to the invention is generally used in a solvent, which can be any conventional solvent for halogenation, and particularly for fluorination. Non-limiting examples of such solvents include DMSO, DMF, CH$_3$CN and THF.

The fluorination step of the method according to the invention can be carried out under conditions known to one of ordinary skill in the art, with heating generally at a temperature comprised between 50 and 145° C., especially comprised between 50 et 100° C., in particular comprised between 55 et 60° C. In this temperature range, the solvent CH$_3$CN has given the best results.

The fluorination step of the method according to the invention is carried out over a time period comprising between 1 and 30 min, especially between 2 and 20 min, in particular between 5 and 10 min and, more particularly over a duration of 8 min.

In a particular embodiment of the invention, the preparation method of a 2-fluoropurine derivative marked with the radioisotope $^{18}$F comprises the following successive steps, involving:

a) reacting a protected 2-nitropurine derivative with a source of [$^{18}$F] marked fluoride ions F to obtain a protected 2-[$^{18}$F]fluoropurine derivative and optionally a partially unprotected 2-[$^{18}$F]fluoropurine derivative.

b) unprotecting said protected 2-[$^{18}$F]fluoro-purine derivative and said partially unprotected 2-[$^{18}$F]fluoro-purine derivative optionally obtained for achieving the 2-[$^{18}$F]fluoropurine derivative.

Using an appropriate protecting group, especially on the purine nucleus and, in particular, two protecting groups on the nitrogen in position 6 of the purine nucleus increases considerably the yield of the marked compounds and reduces the synthesis time. This form of particular embodiment can be represented with the following schematic way (Diagram 3):

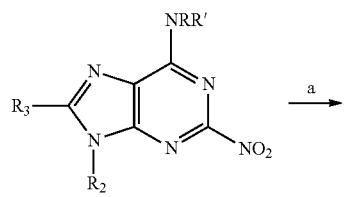

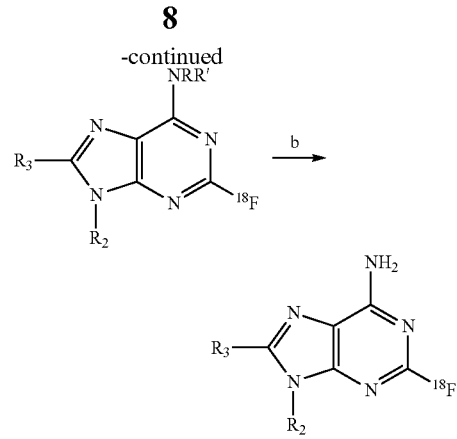

Diagram 3

The protected 2-nitropurine derivative implemented in the context of the present invention has the formula (Ic)

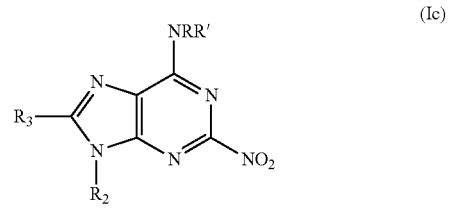

In which R and R' are identical or different protecting groups, and R$_2$ and R$_3$ are as previously defined.

Any adapted protecting group known by one of ordinary skill in the art can be used in the context of the present invention ("Protective groups in Organic Synthesis", P. G. WUTS, T. W. GREEN 3 edition, John Wiley and Sons, 1999).

A protecting group implemented in the context of the present invention is advantageously chosen from among an optionally substituted alkyl group, an optionally substituted acyl group, an optionally substituted aryl group, an optionally substituted benzyl group, an optionally substituted benzoyl group, an electroattractive group, an optionally substituted sulfinyl group, an optionally substituted sulfonyl group, a trityl group, a silyl group, a tert-butoxycarbonyl (BOC) group, a fluorenylmethoxy carbonyl (FMOC) group, and an imide derivative or an imine derivative.

It must be noted that the compounds of formula (Ic) implemented in the context of the present invention comprise at least two protecting groups, which are groups R and R' on the nitrogen in position 6 of the purine nucleus, but can comprise other protecting groups. These other protecting groups are used to protect the groups of the compounds of formula (Ic) that are susceptible to interacting with the source of fluoride ions during fluorination step (a). This aspect is particularly exemplified in the experimental part hereinafter, with the 2-nitropentabenzoyladenosine and the precursor 7. Indeed, these two compounds have three protecting groups in addition to the two protecting groups R and R', these three additional groups protecting the three hydroxyl groups of ribofuranose.

Such compounds of formula (Ic) are easily obtainable by one of ordinary skill in the art. Indeed, the experimental part hereinafter proposes several methods of synthesis allowing for obtaining compounds of formula (Ic) and, more particularly, the 2-nitropentabenzoyladenosine and the precursor 7. It is easy, for one of ordinary skill in the art, to prepare, from this teaching, all the compounds of formula (Ic).

Step (a) of the method according to the invention corresponds to the fluorination step such as defined hereinabove. Consequently, everything which has previously been stated with respect to this fluorination step and particularly concerning the ion fluoride, the counter-ion, the solvent, the temperature and the duration of the fluorination step, also applies to step (a) of the method according to the invention.

The protected 2-[$^{18}$F] fluoropurine derivative obtained after step (a) of the method according to the invention has the formula (Id)

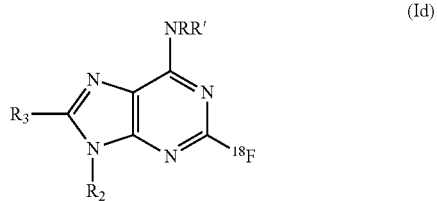

(Id)

with $R_2$, $R_3$, R and R' being as previously defined.

In addition, as a function of the experimental conditions implemented during this fluorination step (a), the protected derivative 2-[$^{18}$F] fluoropurine of formula (Id) can be obtained, after step (a) of the method according to the invention, by mixture with a partially unprotected 2-[$^{18}$F] fluoropurine derivative. The partially unprotected derivative 2-[$^{18}$F] fluoropurine can make up between 0 and 80% of the mixture (protected derivative 2-[$^{18}$F] fluoropurine precursor+partially unprotected derivative 2-[$^{18}$F] fluoropurine) obtained at the end of fluorination step (a). Advantageously, the partially unprotected derivative 2-[$^{18}$F] fluoropurine has the formula (Ie)

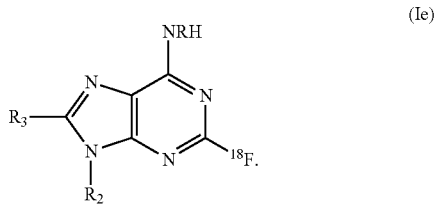

(Ie)

with $R_2$, $R_3$ and R such as previously defined.

The findings of the inventors have particularly shown that, when $K_2SO_4$ is used as a source of cations during the fluorination step (a), the derivative of formula (Ie) is mostly obtained.

Consequently, the present invention also relates to the use of $K_2SO_4$ to prepare, by direct fluorination, a partially unprotected 2-[$^{18}$F] fluoropurine derivative having the formula (Ic) such as previously defined.

The implementation of step (b) of the method according to the invention can have two alternatives.

In a first alternative, this deprotection step (b) is carried out in only one step allowing for passing, without an intermediate, from the compound of formula (Id), optionally mixed with the partially unprotected compound of formula (Ie), to the 2-[$^{18}$F] fluoropurine derivative of formula (It).

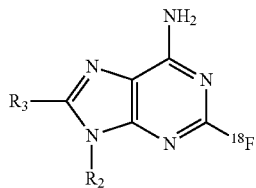

(If)

with $R_2$ and $R_3$ being as previously defined.

In this alternative, the elimination of the protecting groups of the amine function in position 6 of the purine nucleus, i.e. the deprotection, to provide the compound of formula (If) in which the amino group is free, can be carried out by any deprotection method known by one of ordinary skill in the art. The latter will know, as a function of the protected group or groups that are employed, how to choose the most appropriate method of deprotection.

Advantageously, deprotection step (b) is carried out by reacting the protected 2-[$^{18}$F] fluoropurine derivative such as the compound of formula (Id), and the optionally partially unprotected 2-[$^{18}$F] fluoropurine derivative such as the compound of formula (Ie), with a mixture of alcohol and aqueous ammonia. More particularly, deprotection step (b) is carried out by reacting the protected 2-[$^{18}$F] fluoropurine derivative and the optionally present partially unprotected 2-[$^{18}$F] fluoropurine derivative, optionally with an alcohol such as methanol, followed by aqueous ammonia, then by heating at a temperature between 50 and 90° C., and especially 70° C., for a duration comprising between 5 and 45 min, especially between 10 and 30 min and, in particular for 20 min. The ratio mixture (alcohol+aqueous ammonia)/water (v/v) is between 10 and 50%, especially 20 and 40% and, in particular 28%. In the mixture (alcohol+aqueous ammonia), the alcohol/aqueous ammonia proportions given in volume are comprised between 5/1 and 1/5, particularly 2/1 and 1/2 and, in particular 1/1. When the compound of formula (Id) is the 2-fluoro-pentabenzoyladenosine marked with the radioisotope $^{18}$F, better results are usually obtained if the temperature is maintained at less than 80 OC for a reaction time of 20 min.

In a second alternative, this deprotection step (b) is carried out in two sub-steps (b') and (b").

In this alternative, step (b') involves reacting the protected 2-fluoropurine derivative marked with the radioisotope $^{18}$F of formula (Id), obtained from fluorination step (a), with a nucleophilic compound to obtain a mono-hydrolyzed (or mono-deprotected) 2-fluoropurine derivative marked with the radioisotope $^{18}$F of formula (Ie) such as previously defined.

The nucleophilic compound advantageously implemented during sub-step (b') is chosen from among the compounds comprising at least one nitrogen atom carrying a free doublet included in an aromatic, unsaturated, or saturated ring, said ring preferably comprising between 3 and 8 atoms; the primary or secondary amines such as the 2-phenylethylamine; a hydrazine or hydrazone derivative; an amide; a sulfonamide; a urea derivative; a heterocyclic derivative, preferably nitrogenous and/or sulfurated; an alcohol; and a phenol derivative. Nowak et al., *J. Org. Chem.* 70, 2005, 7455-7458 and Ishidoet et al., *J. Chem. Soc.*, Perkin Trans. 1, 1977, 657-660, describe certain nucleophilic compounds hereinabove cited and their uses.

Sub-step (b') of the method according to the invention is generally conducted in a solvent, which can be any conventional solvent known by one of ordinary skill in the art. Non limiting examples of such solvents include DMSO, DMF, CH$_3$CN and THF. Advantageously, the solvent used during sub-step (b') is identical to the solvent used during step (a) of the method of the invention.

Sub-step (b') of the method according to the invention can be conducted under the conditions known to one of ordinary skill in the art, with heating generally at a temperature between 40 and 100° C., especially between 50 and 80° C., in particular on the order of 60° C.

Sub-step (b') of the method according to the invention is carried out over a duration comprising between 1 and 45 min, especially between 2 and 30 min, in particular between 5 and 20 min and, more particularly over duration of 10 min.

No modification has to be made to the conditions of sub-step (b') of the method such as defined hereinabove in the case where a compound of formula (Ie) is already present in the mixture with the compound of formula (Id) after fluorination step (a).

In a second alternative, sub-step (b") is a deprotection whose purpose is to eliminate the remaining protecting group(s). This sub-step (b") can be implemented by any deprotection method known from one having ordinary skill in the art. The latter will know, as a function of the remaining group(s), how to choose the most appropriate deprotection method. However, it must be emphasized that, considering previously implemented step (b'), the conditions during the deprotection sub-step (b") can be more drastic than the conditions used during the deprotection according to the first alternative (step (b)), particularly in terms of temperature of reaction.

By way of non-limiting examples, when the protecting groups are benzoyl groups, the sub-step (b") can be implemented by reacting the compound of the formula (Ie) with an alcohol such as methanol, followed by aqueous ammonia, then heating at a temperature comprised between 50 and 110° C., especially comprised between 70 and 90° C., and in particular comprised between 80 and 85° C., for a period comprised between 5 and 45 min, especially between 10 and 30 min, and in particular 20 min.

In the context of the method according to the invention, the deprotection steps (b) and (b") are followed by a hydrolysis step. Any hydrolysis technique known by one having ordinary skill in the art can be implemented in the context of the present invention. By way of non-limiting examples, mention may be made of a hydrolysis conducted with an aqueous solution of acetic acid, or of an elution via an acid resin.

The purification of the 2-fluoropurine derivative marked with the radioisotope $^{18}$F following the method of the invention can be carried out, if necessary, by any purification technique know by one having ordinary skill in the art. By way of non-limiting examples, mention may be made of chromatography, flash chromatography, flash chromatography on silica gel, a semi-preparative HPLC, etc.

The method according to the invention is simple, reliable, easy to implement, and can be easily robotized.

The nucleophilic substitution of a 2-nitropurine derivative—which can be, if necessary, protected—with fluoride ions in the form of [$^{18}$F]-KF or [$^{18}$F]-Bu$_4$NF leads, after deprotection and purification with the radiomarked 2-fluoropurine derivative to a global high yield.

The incorporation of fluor-18 halogen allowing for obtaining protected 2-nitropurine derivatives is carried out in a very efficient manner with a high yield, for example on the order of 70 to 100%, especially 80 to 100%, and more particularly 90 to 98%. The invention also includes the possibility of obtaining, in a selective manner and with a high yield, a deprotected radiomarked 2-fluoro-purine derivative.

The final yield of the entire method for a purified product is extremely high, for example on the order of 40-60% and this, no matter the alternative of the method that is used. It must be emphasized that the presence, or lack thereof, of a partially deprotected 2-[$^{18}$F] fluoropurine of the formula (Ie) following step (a) of fluorination, does not affect the final yield of the method according to the invention.

Examples of application describe the synthesis of the [$^{18}$F]-2-fluoroadenosine and of the [$^{18}$F]-fludarabine via a fluorination with [$^{18}$F] and a deprotection. In comparison with other methods, the improved yields are obtained from easily obtainable intermediates with a short reaction time, including the purification, which makes the method of the invention compatible with a PET study.

Indeed, the overall duration of the method according to the invention is short: by way of example, it generally takes between 60 and 120 min, preferably 75 to 85 min.

The present invention also relates to a method for preparing a mono-hydrolyzed (or mono-protected) 2-fluoropurine derivative marked with a radioisotope $^{18}$F of the formula (Ie) such as previously disclosed. Said method involves reacting a protected 2-fluoropurine derivative marked with the radioisotope $^{18}$F of formula (Id) such as previously disclosed, with a nucleophile compound such as previously disclosed under the conditions previously disclosed for sub-step (b').

The present invention also relates to a compound that can be prepared with a method according to the present invention or to be obtained during the method according to the present invention (reaction intermediate).

Advantageously, a compound according to the present invention is a compound of the formula (A)

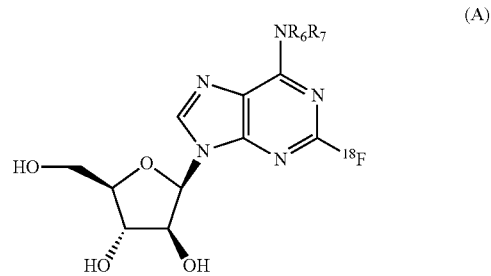

(A)

in which R$_6$ and R$_7$ are independently H or a protecting group, or a salt thereof.

The present invention also relates to a compound of the formula (A) having, in addition, a mono-, di- ou tri-phosphate group, said group being advantageously in the 5 position of the ribose.

Among the compounds of the invention, the following compounds are particularly preferred:

the fludarabine marked with the radioisotope $^{18}$F of the formula (B) or one of its salts

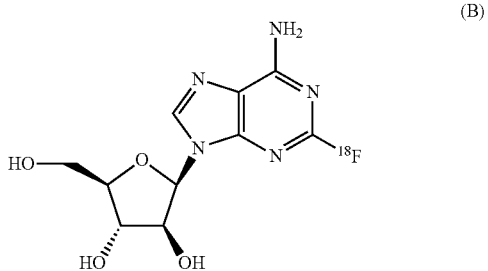 [SMILES: Nc1nc([18F])nc2c1ncn2[C@@H]1O[C@H](CO)[C@@H](O)[C@@H]1O]

the fludarabine phosphate marked with the radioisotope $^{18}F$ of the formula (C) or one of its salts

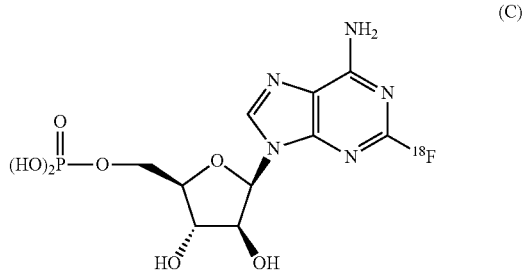

In the context of the invention, "salt" refers to acid addition salts and base addition salts. Such salts can be formed by conventional means, for example by reaction of a form of free acid or a form of free base of a compound of the invention with one or several equivalents of an appropriate acid or base, optionally in a solvent, or in a medium in which the salt is insoluble, then by extracting said solvent, or said medium, by using conventional techniques (for example in vacuum or by freeze drying). The salts can also be prepared by replacing a counter-ion of a compound of the invention in the form of a salt with another counter-ion, for example by using an appropriate ion-exchange resin.

Especially in the purpose of being administered to a human or animal body, the salts of compounds according to the invention are advantageously pharmaceutically acceptable salts.

In particular, when the compounds according to the invention are in the form of a salt, the latter being a salt of an alkali metal, in particular sodium or potassium salt, or salt of alkaline earth metal, in particular magnesium or calcium, or even a salt with an organic amide, more particularly with an amino acid such as arginine or lysine.

When the compounds according to the invention have an amine function and are in the form of a salt of this amine, the salt is a salt of inorganic acid such as, for example, hydrochloric acid, sulfuric acid, or hydrobromic acid, or in the form of an organic salt, such as, for example, acetic acid, triflic acid, tartatic acid, oxalic acid, citric acid, trifluoroacetic acid, or methanesulfonic acid.

The present invention additionally relates to a pharmaceutical composition or a diagnostic composition comprising at least one compound according to the invention such as previously disclosed, in an acceptable pharmaceutical vehicle.

In the context of the present invention, "acceptable pharmaceutical vehicle" refers to one or several conventional pharmaceutical additives, excipients, buffers, thinners, and/or auxiliary agent known by one having ordinary skill in the art.

The compounds and compositions according to the present invention can be used for PET imaging studies, and more particularly, for PET imaging studies applied to the fields of neurobiology, cardiology, oncology, and more particularly, to the fields of chronic lymphoid leukemia and related illnesses.

The compounds and compositions according to the present invention can be used for the treatment evaluation of the chronic lymphoid leukemia and for the in vivo mapping of malignant hematopoietic cells.

The non-limiting examples herein below describe the method and the products according to the present invention, with reference to the annexed drawings.

DETAILED EXPLANATION OF THE PARTICULAR EMBODIMENTS

Material and Methods

Figure 1A:
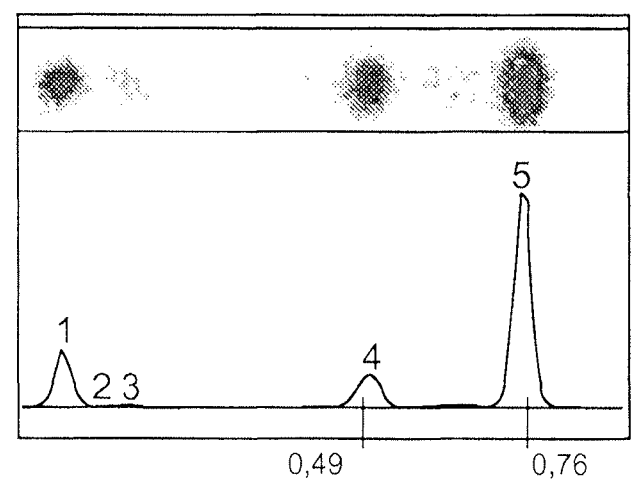
FIG. 1A shows the radio-thin-layer chromatographies (or "RTLC") obtained, at t=5 min, from a fluorination reaction mixture using as a source of cations $K_2CO_1$.
Figure 1A:
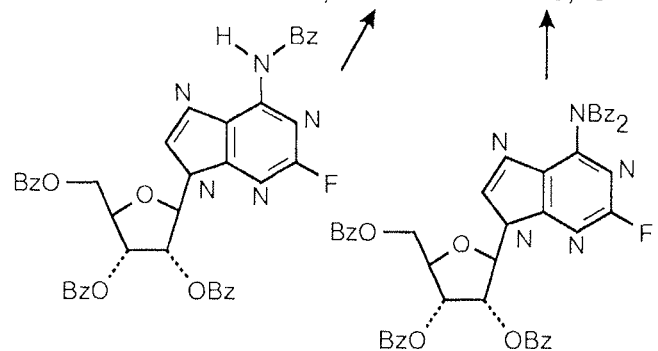
Figure 1B:
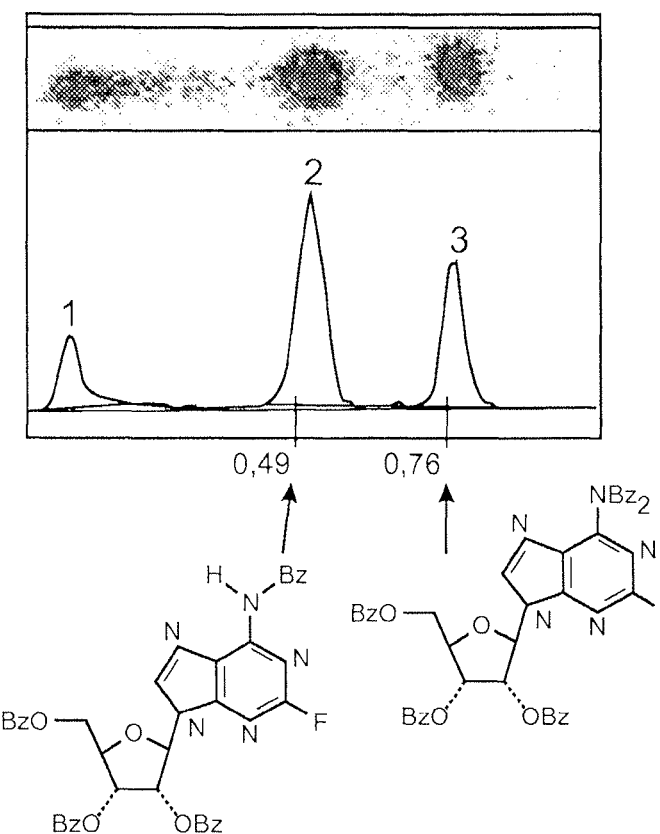
FIG. 1B shows the radio-thin-layer chromatographies (or "RTLC") obtained, at t=5 min, from a fluorination reaction mixture using as a source of cations $K_2SO_4$.

In general, all the chemical products and solvents are of ACS quality (Analytical grade chemical solvent) or of HPLC (High-Performance Liquid Chromatography) quality and are used without any other purification, unless otherwise specified.

Dichloromethane ($CH_2Cl_2$) has been distilled over $P_2O_5$. Pyridine was dried and distilled on KOH. Acetonitrile, DMF, THF, Dioxane are purified on resin on a Millipore apparatus and filtered with a 0.22 µm filter (Millipak). The fludarabine (2F-ARA-A) was obtained from Sigma.

HPLC analyses were carried out with an HPLC pump (model: L-6200 Intelligent Pump, Merck), a U.V. detector Merck L-4250 ($\lambda$=254 nm) in series with a flux $\beta$ detector by Novelec. HPLC chromatograms were recorded by a dual-channel interface/module (Varian star 800) connected to a PC provided with the Galaxy software (Varian).

Thin layer chromatographies (TLC) were made on silica plates (gel 60 $F_{254}$) and visualized using an U.V. lamp ($\lambda$=254 nm) or by immersion in an appropriate coloration agent ($KMnO_4$, Vanillin, Iodine or PMA) followed by gentle heating. The radioactive compounds were localized on the TLC using an imager (Packard Instant Imager) connected to a PC.

Flash chromatographies were made on columns of silica gel ($SiO_2$ 40-63 µm, Merck).

NMR (Nuclear Magnetic Resonance): NMR $^1H$ spectra were recorded using a Bruker apparatus at 250 or 400 MHz (DPX 250 or DRX 400). Chemical shifts δ are indicated in ppm using the TMS as reference. Coupling constants J are given in Hertz (Hz). The multiplicities are indicated using the following abbreviations: s=singulet, d=doublet, t=triplet, q=quartet, m=multiplet, bs=broad singulet.

$^{13}C$ {$^{1}H$} NMP spectra were recorded using a Broker apparatus at 62.9 or 100.6 MHz. Chemical shifts δ are indicated in ppm using deuterated solvent as reference. Coupling constants J are given in Hertz (Hz).

$^{19}F$ RMN spectra were recorded using a Brüker apparatus (Advanced DRX 400), (376 MHz). Chemical shifts δ are indicated in ppm using the $CFCl_3$ as external reference.

The fluoride ion [$^{18}F$]$F^-$ in water was obtained from a cyclotron (IBA, Cyclone 18/9 RF) using a proton beam on 95% [$^{18}O$] enriched water (Cambridge Isotope Laboratories Inc.). The fluoride ion [$^{18}F$]$F^-$ in water was purified on a QMA ion-exchange resin (ABX, Advanced biochemical compounds) eluted with 500 μl of aqueous $K_2CO_3$ (1 mg/ml to 5 mg/ml).

Water was evaporated by azeotropic distillation with acetonitrile at 110° C. using a nitrogen stream using stirring/heating module (Pierce).

Radioactivity measurements were carried out using a Capintec CRC-15 dose calibrator.

Example 1

Preparation of [$^{18}F$]Fluoroadenosine

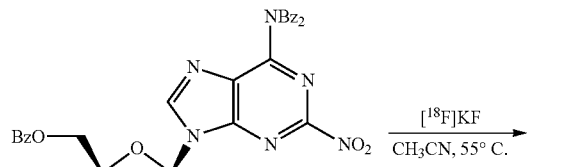

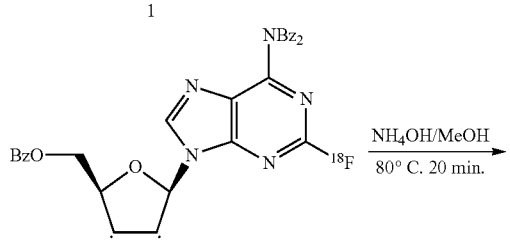

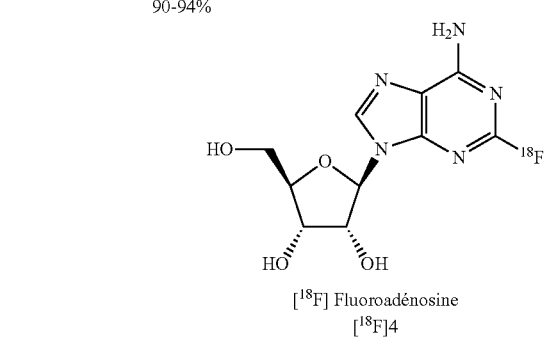

Diagram 4

Chemistry

Pentabenzoyled adenosine and the 2-nitro-pentabenzoyladenosine 1 were prepared according to the methods previously described (Article of Braendvang et al., 2006, *Synthesis*, 18, 2993 and International Application WO 2005/056571) and purified by silica gel chromatography.

Protected 2-fluoro-adenosine 2 and 3 were obtained according to the modified protocol (1.1 equivalent of $Bu_4NF$ in the $CH_3CN$ instead of an excess of reactant in DMF) enabling their isolation in high yields.

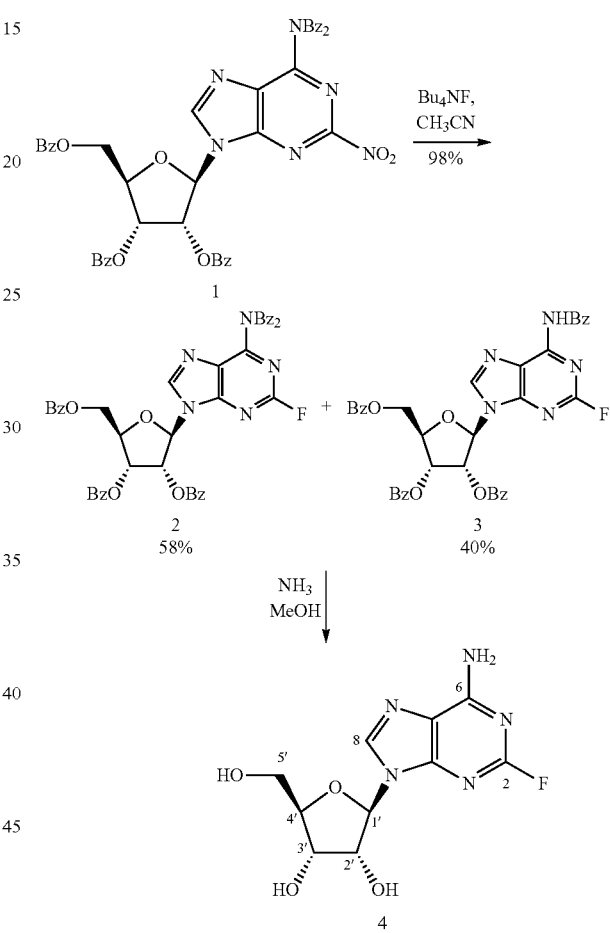

Diagram 5

Tetrabutylammonium fluoride (TBAF) (1.3 eq, 600 μL, 0.6 mmol, 1 M in THF) has been added drop wise for 1 min to a suspension of 2-nitro-adenosine 1 (379 mg, 0.45 mmol) in dry acetonitrile (15 mL) at 0° C. The mixture was stirred for 20 min and the resulting solution was vacuum evaporated without heating. The product has been purified by flash chromatography ($CH_2Cl_2$-acetone). The compounds 2 and 3 have been isolated with a yield of 58% (211 mg) and 35% (130 mg), respectively.

A solution of the protected compound 2 (185 mg, 0.23 mmol) in MeOH (40 mL) was saturated by a stream of ammoniac gaz for 15 min at 0° C. The resulting mixture was stirred for 14 hours at room temperature, then evaporated under reduced pressure and purified by flash silica gel chromatography (AcOEt-MeOH 83:17) to give 51 mg (77%) of 2-fluoroadenosine 4.

2-fluoro-6-N,N-dibenzoyl-9-(2',3',5'-tri-O-benzoyl-β-D-ribofuranosyl)-9H-purine 2

$^1$H NMR (400 MHz, CDCl$_3$): δ=4.82 (m, 3H, H$_4$, H$_{5'}$); 6.17 (t, 1H, H$_{3'}$, J=5.4 Hz); 6.22 (t, 1H, H$_{2'}$, J=5.8 Hz); 6.46 (d, 1H, H$_{1'}$, J=5.3 Hz); 7.28-7.52 (m, 15H, Ar); 7.85 (dd, 4H, J=1.2 and 8.4 Hz; H$_{Ar}$); 7.95 (dd, 2H, J=1.2 and 8.4 Hz, H$_{Ar}$); 8.02 (dd, 2H, J=1.2 et 8.4 Hz, H$_{Ar}$); 8.12 (dd, 2H, J=1.2 et 8.40, H$_{Ar}$); 8.20 (s, 1H, H$_8$).
$^{13}$C NMR (100.6 MHz, CDCl$_3$): δ=63.9 (C$_{5'}$); 71.7 (C$_{4'}$); 74.4 (C$_{3'}$); 81.4 (C$_{2'}$); 87.0 (C$_{1'}$); 126.4 (d, J$_{CF}$=5.0 Hz, C$_5$); 128.7; 128.9; 129.0; 129.1; 129.3; 129.5; 129.9; 130.1; 130.2; 130.3; 133.7; 133.9; 134.0; 134.2; 134.3; 143.7 (d, J$_F$=3.8 Hz, C$_8$); 154.3 (d, J$_{CF}$=16.9 Hz, C$_6$); 154.9 (d, J$_{CF}$=17.0 Hz, C$_4$); 158.3 (d, J$_{CF}$=218.9 Hz, C$_2$); 165.5 (C=O); 165.7 (C=O); 166.5 (C=O); 172.1 (2×C=O).
$^{19}$F NMR (376.5 MHz, CDCl$_3$): δ=−49.1

2-fluoro-6-N-benzoyl-9-(2',3',5'-tri-O-benzoyl-β-D-ribofuranosyl)-9H-purine 3

(two rotamers: ratio 80/20).
$^1$H NMR (400 MHz, CDCl$_3$): δ=4.74 (m, 3.6H, H$_4$, H$_{5'}$); 6.12 (m, 2.4H, H$_3$, H$_{2'}$); 6.39 (d, 0.8H, H$_{1'}$, J=5.5 Hz); 6.51 (d, 0.2H, H$_{1'}$, J=5.5 Hz); 7.28-7.51 (m, 15H, H$_{Ar}$); 7.83-8.01 (m, 10H, H$_{Ar}$); 8.08 (s, 0.8H, H$_8$); 8.39 (s, 0.2H, H$_8$); 8.94 (s, 0.8H, NH); 9.14 (s, 0.2H, NH).
$^{19}$F NMR (376.5 MHz, CDCl$_3$): δ=−47.6

2-fluoro-9-(β-D-ribofuranosyl)-9H-purine 4

$^1$H NMR (400 MHz, DMSO-D$_6$): δ=3.60 (m, 2H, H$_{5'}$); 3.94 (m, 1H, H$_{4'}$); 4.13 (m, 1H, H$_{3'}$); 4.52 (m, 1H, H$_{2'}$); 5.07 (t, 1H, OH-5', J=5.6 Hz); 5.20 (d, 1H, OH-3', J=4.7 Hz); 5.47 (d, 1H, OH-2', J=5.9 Hz); 5.79 (d, 1H, H$_{1'}$, J=5.9 Hz); 7.87 (bs, 2H, NH$_2$); 8.35 (s, 1H, H$_8$).
$^{19}$F NMR (376.5 MHz, DMSO-D$_6$): δ=−52.5

Radiochemistry

Method A

The ion fluoride [$^{18}$F]F$^−$ in water was adsorbed on a QMA (ABX) ion-exchange resin and eluted with aqueous (500 μL, 1 mg/mL) K$_2$CO$_3$ and Kryptofix (K$_{222}$, 15-25 mg) in acetonitrile (500 μL). Water was evaporated under a nitrogen stream at 110° C. by azeotropic distillation using acetonitrile (3×1 mL). The precursor 1 (5-5.5 mg in 500-800 μL of acetonitrile) was added to the dry [$^{18}$F]KF complex. Heating at 55-60° C. for 5 to 10 min (preferably 8 min) provided the expected [$^{18}$F] fluoroadenosine 2 in a radiochemical yield of more than 90% (thin-layer chromatography SiO$_2$ eluted with CH$_2$Cl$_2$/acetone 95/5, Packard instant imager). The solution was diluted with 500 μL of ethyl acetate (AcOEt) and adsorbed on a silica cartridge Sep-Pak (WATERS). Elution with 3-3.5 mL of AcOEt followed by 5 mL of dry air with the evaporation of the solvent has made it possible to provide the protected [$^{18}$F]2-fluoroadenosine 2 with a overall yield of 86% (decay corrected) from [$^{18}$F]KF.

Deprotection was carried out in a conventional manner by the addition of 500 μL of methanol followed by 500 μL of aqueous ammonia (29% in water) and heating at 65-70° C. for 20 min. After cooling, acetic acid (0.7 mL, 40% in water or 0.3 ml of pure acetic acid) was added and the clear solution was purified by a semi-preparative HPLC chromatography on a μBondapak column (water/ethanol 97/3 5 mL/min) to obtain the [$^{18}$F]-fluoroadenosine 4 with a overall yield of 50% (decay corrected).

Method B

The B method is an alternative to selectively obtain the mono-hydrolyzed fluoroadenosine [$^{18}$F] 3. Subsequent deprotection can be carried out using more drastic conditions (80-85° C.) to obtain the [$^{18}$F]-fluoroadenosine 4 and this strategy improves the deprotection step (90%).

2-phenyl-ethylamine (1 mg) in 100 μL of acetonitrile was added to the crude [$^{18}$F] fluoroadenosine 2 in acetonitrile (obtained according to method A) and the solution was heated for 10 min at 60° C. A TLC and HPLC analysis indicated a quantitative formation of the intermediate marked/labelled mono-deprotected that is the compound [$^{18}$F] 3. The solution was diluted with 500 μL of AcOEt and adsorbed on a silica Sep-Pak cartridge (WATERS). Elution with 3.5 mL of AcOEt followed by 5 mL of dry air and the evaporation of the solvent makes it possible to obtain the compound [$^{18}$F] 3 with a 60% non-optimized yield (decay corrected).

Final deprotection was carried out by adding 500 μL of methanol followed by 400 μL of ammonia (29% in water) and heating at 80-85° C. for 20 min. After cooling, acetic acid (0.7 mL, 40% in the water) was added and the clear solution was purified by a semi-preparative HPLC chromatography on a μBondapak column (water/ethanol 97/3, 5 mL/min) to produce the marked/labelled 2-fluoroadenosine [$^{18}$F] 4.

Example 2

Preparation of [$^{18}$F]Fludarabine

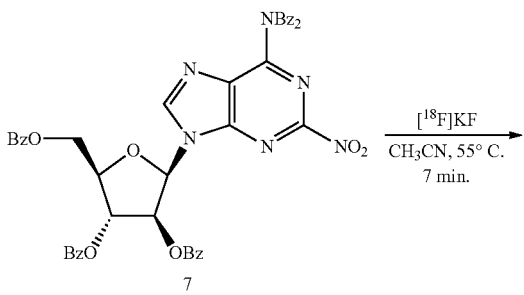

jusqu'à 98%

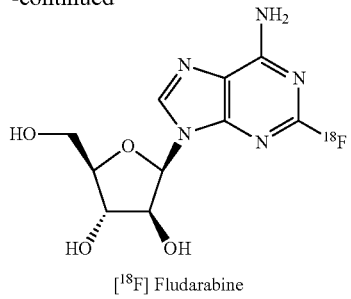

[18F] Fludarabine

Diagram 6: Synthesis of the [18F]Fludarabine

Chemistry

Synthesis of the precursor 7 can be achieved through protection and nitration of the 9(β-D-arabinofuranosyl)-9H-purine according to the protocols described for its ribose analogue (Article of Braendvang et al., 2006, Synthesis, 18, 2993 and international application WO 2005/056571).

Alternatively, compound 7 can also be obtained from the adenosine or the guanosine (diagram 6) (Article of Gimisis et al., 1998, Tetrahedron, 54, 573 and international application WO 9412514).

Synthesis of the 6-N,N-dibenzoyl-9-(2',3',5'-tri-O-benzoyl-β-D-arabinofuranosyl)-9H-purine 6

Benzoyl chloride (750 µL, 6.49 mmol) was added to a solution of the compound 5 (181 mg, 0.82 mmol) in the anhydrous pyridine (7 mL) and the mixture was refluxed for 6 hours. After cooling and extraction ($CH_2Cl_2$), the organic phase was washed with saturated aqueous $NaHCO_3$ (10 mL) and brine (2×10 mL), and dried over $Na_2SO_4$. Filtration and evaporation under reduced pressure yielded the crude product as a pale yellow solid, which was purified by flash chromatography ($CH_2Cl_2$: acetone, 95:5) to yield 606 mg (96%) of 6.

$^1$H NMR (250 MHz, $CDCl_3$): δ=4.73 (m, 3H, $H_{4'}$ and $H_{5'}$); 5.91 (m, 2H, $H_{3'}$ and $H_{2'}$); 6.48 (d, 1H, $H_{1'}$, J=4.2 Hz); 7.20-7.39 (m, 15H, $H_{Ar}$); 7.68-7.72 (m, 5H, $H_{Ar}$); 7.96-8.00 (m, 5H, $H_{Ar}$); 8.38 (s, 1H, $H_2$); 8.58 (s, 1H, $H_8$).

6-N, N-dibenzoyl-9-(2',3',5'-tri-O-benzoyl-β-D-arabinofuranosyl)-2-nitro-9H-purine 7

A nitrated mixture was prepared by adding 2,2,2-trifluoroacetic anhydride (160 µL, 1.15 mmol) for 2 min to a solution of tetrabutylammonium nitrate (351 mg, 1.15 mmol) in dry methylene chloride (15 mL) at 0° C. After 45 min, the solution was added to 6 (606 mg, 0.77 mmol) in dry

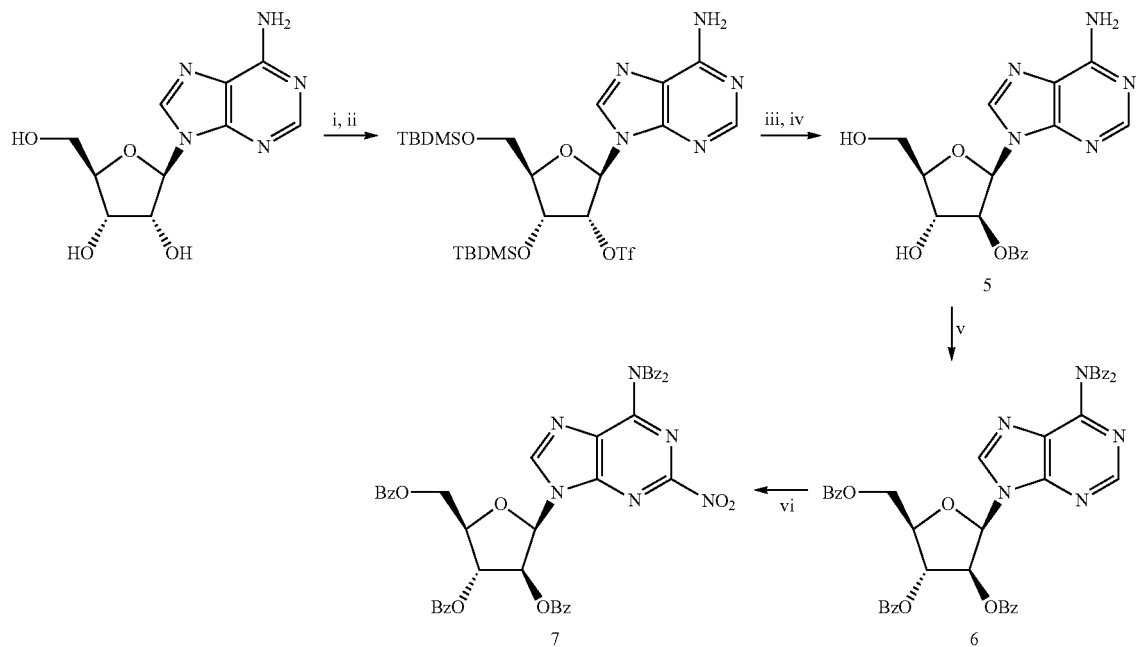

Diagram 7: Synthesis of Precursor 7

The reactants and yields of the different steps for the synthesis of the precursor 7 (diagram 7) are:

i: TBDMSCl, DABCO, $AgNO_3$, THF, 53%.
ii: $Tf_2O$, DMAP, DIPEA, Py. 67%.
iii: PhCOOK, DMSO, 96%.
iv: $Bu_4NF$, THF, 81%.
v: PhCOCl, Py, 95%.
vi: TBAN, TFAA, $CH_2Cl_2$, 45%.

methylene chloride (15 mL) at 0° C. After 14 hours at room temperature (and protected from light), the reaction mixture was poured into a cold mixture of water (30 mL), saturated aqueous $NaHCO_3$ (20 mL) and $CH_2Cl_2$-$Et_2O$ (1:2, 20 mL). The aqueous layer was extracted from $CH_2Cl_2$-$Et_2O$ (1:2, 2×20 mL). The combined organic extracts was washed with brine (2×20 mL), dried ($Na_2SO_4$), and vacuum evaporated (without heating above 40° C.). The product was purified by flash chromatography ($CH_2Cl_2$-acetone 95:5) to produce 201 mg (45%) of 7.

$^1$H NMR (250 MHz, $CDCl_3$): δ=4.79 (m, 3H, $H_{4'}$, $H_{5'}$); 5.86 (m, 2H, $H_{3'}$, $H_{2'}$); 6.83 (d, 1H, $H_{1'}$, J=5.1 Hz); 7.21-7.47

(m, 15H, H$_{Ar}$); 7.66-7.73 (m, 6H, H$_{Ar}$); 7.95 (dd, 2H, J=1.4 and 7.8 Hz, H$_{Ar}$); 8.05 (dd, 2H, J=1.4 and 7.8 Hz, H$_{Ar}$); 8.52 (s, 1H, H$_8$).

$^{13}$C NMR (62.9 MHz, CDCl$_3$): δ=63.5 (C$_{5'}$); 76.3 (C$_{2'}$); 77.1 (C$_{3'}$); 81.6 (C$_{4'}$); 84.7 (C$_{1'}$); 127.8 (C$_5$); 128.6; 128.9; 129.1; 129.2; 129.3; 129.5; 129.6; 129.8; 130.1; 130.2; 130.5; 133.7; 133.8; 133.9; 134.5; 134.6; 147.7 (C$_8$); 153.0 (C$_6$); 153.1 (C$_2$); 154.0 (C$_4$); 165.1 (C=O); 165.8 (C=O); 166.6 (C=O); 171.8 (2×C=O).

Radiochemistry

[18F]-FLUDARABINE:

Using 4.8 to 5.5 mg de 6-N,N-dibenzoyl-9-(2',3',5'-tri-O-benzoyl-β-D-arabinofuranosyl)-2-nitro-9H-purine 7 and the methods (A or B) previously described, the [$^{18}$F]-fludarabine has been obtained with an overall radiochemical yield of 63% (decay corrected) in about 85 min after the semi-preparative HPLC purification (Water/Ethanol 97/3 5 mL/min).

Example 3

Evolution of the Fluorination Reaction Mixture as a Function of the Potassium Salt Used as Source of Cations Fluorination reaction is carried out in DMSO at 140° C. in presence of potassium salt (K$_2$CO$_3$, 0.5-1 mg or K$_2$SO$_4$ 3-5 mg) and kryptofix K2.2.2 (20 mg) using 5 mg of precursor (2-nitro purine). Reaction products obtained present the following structure:

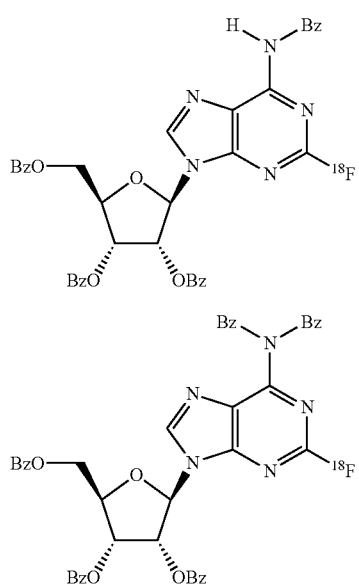

Analysis of the reaction mixture is made by radio-TLC (SiO$_2$, eluted CH$_2$Cl$_2$/Acetone 95/5) from a 15-25 μL sampling taken every 5 min.

Radioactive products are identified by co-elution with non-radioactive references (product 1 Rf=0.49; product 2 Rf=0.75; cf Drawing 1).

Figure 2:
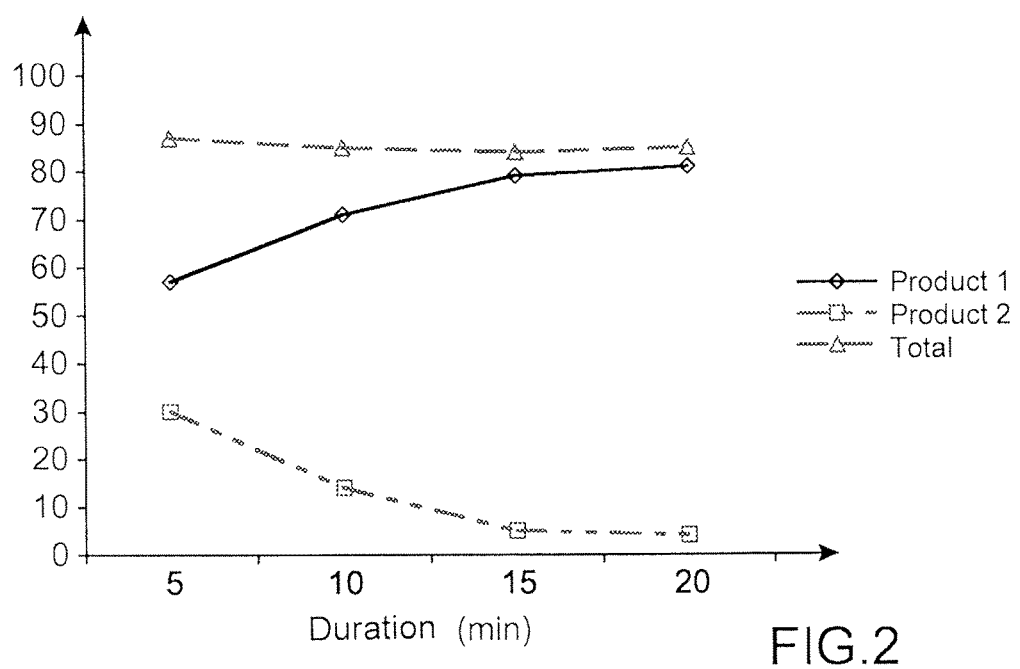
FIG. 2 shows the evolution as a function of the duration of the reaction mixture composition during the fluorination step using $K_2SO_4$ as a source of cations.

FIG. 2 shows that in K$_2$SO$_4$ presence, the product 1 (partially deprotected) is majoritarily formed during the fluorination reaction. The composition of the mixture evolves as a function of time and product 1 becomes largely majoritary after 15 min to the detriment of product 2 (progressive deprotection of product 2 in these reaction conditions).

Figure 3:
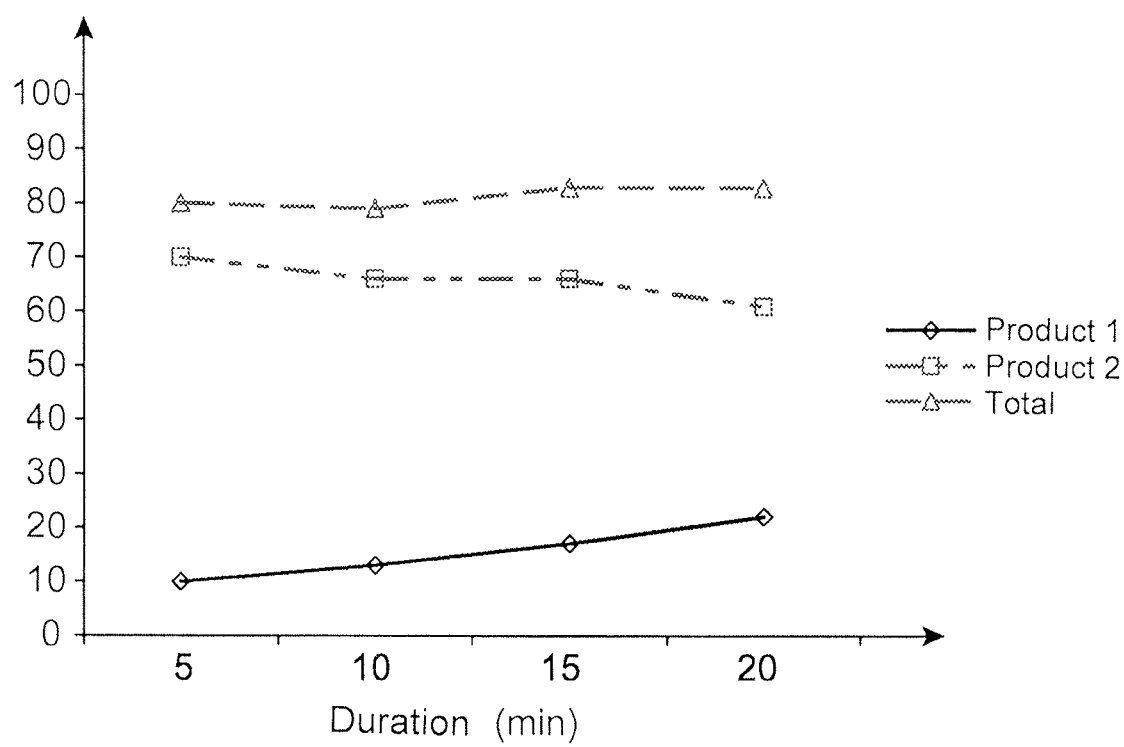
FIG. 3 shows the evolution as a function of the duration of the reaction mixture composition during the fluorination step using $K_2CO_3$ as a source of cations.

When the fluorination reaction is carried out in K$_2$CO$_3$ presence, product 2 (entirely protected) is majoritarily formed and its proportion remains stable over time (61 to 70%), as shown in FIG. 3.

Figure 4:
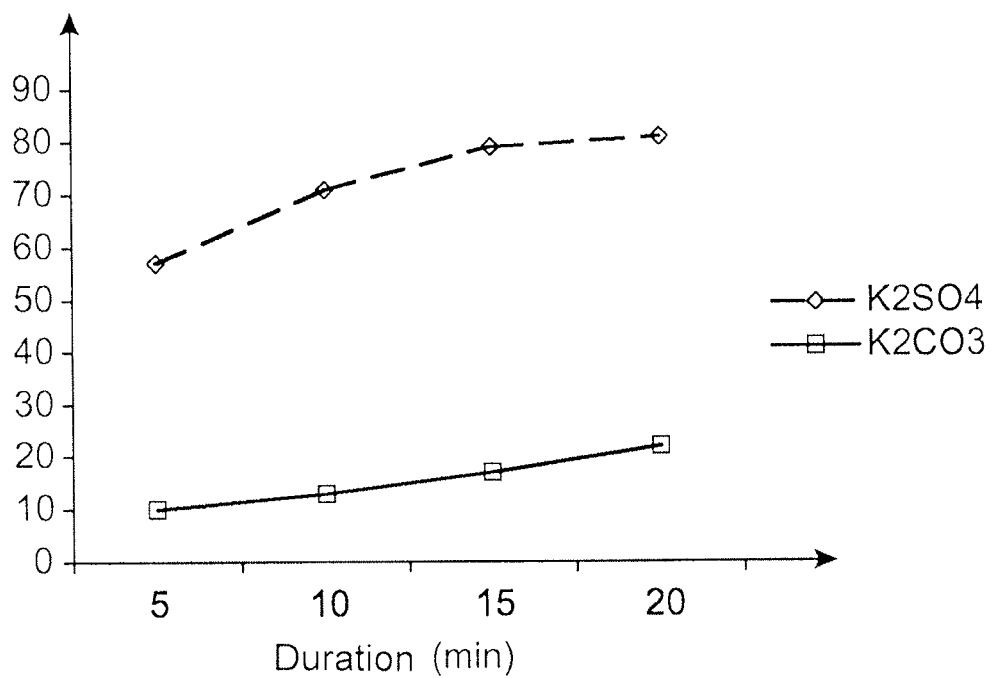
FIG. 4 shows the comparison of the percentages of the partially deprotected product in the reactional environment as a function of the time and the nature of the potassium salt used as a source of cations ($K_2SO_4$ or $K_2CO_3$).

FIG. 4 makes it possible to observe the influence of potassium salt nature (K$_2$SO$_4$ versus K$_2$CO$_3$) on the formation of product 1. Using K$_2$SO$_4$ makes it possible to majoritarily obtain product 1 and after 20 min of reaction, product 1 represents 95% (ratio 1/2=81/4) of the fluorination products.

BIBLIOGRAPHICAL REFERENCES

Article of Jacobson K. A. and Gao Z.-G. *Nat. Rev. Drug Discovery* 2006, 5, 247;
International Application WO 03/099342;
Article of Robins M. J. and Uznanski B., 1981, *Can. J. Chem.* 59, 2608;
Article of Horti et al., 2006, *J. Labelled Compd. Radiopharm.*, 49, 811;
International Application WO 2005/044312;
Article of Hocek et al., 2005, *Eur. J. Org. Chem.* 14, 3026;
Patent Application EP 1 956 013;
Article of Irie et al., 1982, *Int. J. Appl. Radial. Isot.* 33(6), 445;
International Application WO 2005/056571;
Article of Wanner et al., *Med. Chem. Lett.* 10, 2000b, 2141-2144;
Article of Wanner and Koomen, *J. Chem. Soc., Perkin Trans 1*, 2001, 1908-1915;
Article of Degati et al., *Tetrahedron lett.*, 41, 2000, 1291-1295;
Article of Nowak et al., *J. Org Chem.* 70, 2005, 7455-7458;
Article of Ishido et al., *J. Chem. Soc., Perkin Trans.* 1, 1977, 657-660;
Article of Braendvang et al., 2006, *Synthesis*, 18, 2993;
Article of Gimisis et al., 1998, *Tetrahedron*, 54, 573;
International Application WO 94/12514.

The invention claimed is:

1. A method for performing PET imaging studies in a subject having chronic lymphoid leukemia or a related illness, comprising:
    synthesizing a $^{18}$F-labeled fludarabine corresponding to the formula (B) from a protected 2-nitropurine derivative having the formula (1c)

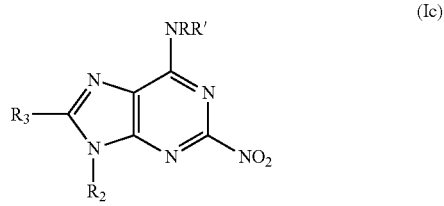

in which
R and R' are identical or different protecting groups;
R$_2$ is hydrogen, an optionally substituted alkyl group, an optionally substituted aryl group, an optionally substituted furanose group, or an optionally substituted pyranose group;

R₃ is hydrogen, an optionally substituted alkyl group, an optionally substituted aryl group, a halogen, a —OR₈ group or a —SR₈ group, with R₈ being hydrogen, an optionally substituted alkyl group or an optionally substituted aryl group, wherein said synthesizing includes the following successive steps of (i) reacting the protected 2-nitropurine derivative having the formula (1c) with a source of [¹⁸F] labeled fluoride ions in a solvent of CH₃CN at a temperature between 55° C. and 60° C. for a duration of between 1 min and 30 min to obtain a protected 2-[¹⁸F] fluoropurine derivative and optionally a partially unprotected 2-[¹⁸F] fluoropurine derivative, and (ii) unprotecting said protected 2-[¹⁸F] fluoropurine derivative and said partially unprotective 2-[¹⁸F] fluoropurine derivative to obtain said ¹⁸F-labeled fludarabine corresponding to the formula (B) with a yield of 40-60%

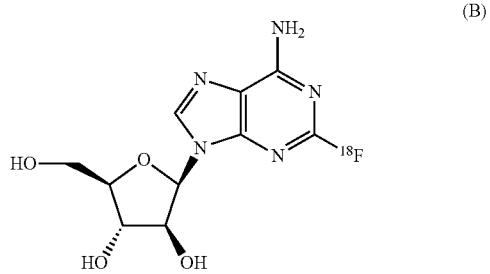 [SMILES: Nc1nc([18F])nc2c1ncn2[C@@H]1O[C@H](CO)[C@@H](O)[C@@H]1O]

(B)

administering to the subject the ¹⁸F-labeled fludarabine of the formula (B) or one of its salts; and detecting said ¹⁸F-labeled fludarabine.

2. The method of claim 1, wherein said ¹⁸F-labeled fludarabine is a PET probe.

3. The method of claim 1, wherein the step (ii) consists of reacting said protected 2-[¹⁸F] fluoropurine derivative and said partially unprotected 2-[¹⁸F] flurpurine derivative with an alcohol, followed by aqueous ammonia and then by heating at a temperature between 50° C. to 90° C. for between 5 min to 45 min.

4. The method of claim 1, wherein said protected 2-[¹⁸F] fluoropurine derivative and optionally the partially unprotected 2-[¹⁸F] fluoropurine derivative are obtained with a yield of 70-100%.

5. A method for performing PET imaging studies on a subject comprising:

synthesizing a ¹⁸F-labeled fludarabine corresponding to the formula (B) from a protected 2-nitropurine derivative having the formula (1c)

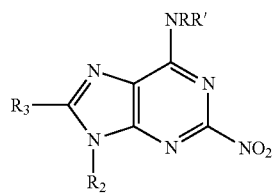

(1c)

in which

R and R' are identical or different protecting groups;

R₂ is hydrogen, an optionally substituted alkyl group, an optionally substituted aryl group, an optionally substituted furanose group, or an optionally substituted pyranose group;

R₃ is hydrogen, an optionally substituted alkyl group, an optionally substituted aryl group, a halogen, a —OR₈ group or a —SR₈ group, with R₈ being hydrogen, an optionally substituted alkyl group or an optionally substituted aryl group, wherein said synthesizing includes the following successive steps of (i) reacting the protected 2-nitropurine derivative having the formula (1c) with a source of [¹⁸F] labeled fluoride ions in a solvent of CH₃CN at a temperature between 55° C. and 60° C. for a duration of between 1 min and 30 min to obtain a protected 2-[¹⁸F] fluoropurine derivative and optionally a partially unprotected 2-[¹⁸F] fluoropurine derivative, and (ii) unprotecting said protected 2-[¹⁸F] fluoropurine derivative and said partially unprotective 2-[¹⁸F] fluoropurine derivative to obtain said ¹⁸F-labeled fludarabine corresponding to the formula (B) with a yield of 40-60%

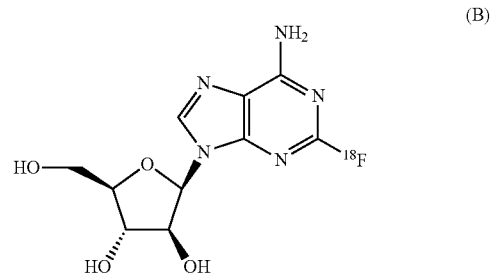 [SMILES: Nc1nc([18F])nc2c1ncn2[C@@H]1O[C@H](CO)[C@@H](O)[C@@H]1O]

(B)

administering to the subject the ¹⁸F-labeled fludarabine of the formula (B) or one of its salts; and detecting said ¹⁸F-labeled fludarabine, wherein said PET imaging studies are used for in vivo mapping of malignant hematopoietic cells.

6. The method of claim 5, wherein the ¹⁸F-labeled fludarabine is a PET probe.

* * * * *